United States Patent [19]
Bonin

[11] Patent Number: 6,026,677
[45] Date of Patent: Feb. 22, 2000

[54] APPARATUS FOR MICROINDENTATION HARDNESS TESTING AND SURFACE IMAGING INCORPORATING A MULTI-PLATE CAPACITOR SYSTEM

[75] Inventor: Wayne A. Bonin, North Oaks, Minn.

[73] Assignee: Hysitron, Incorporated, Edina, Minn.

[ * ] Notice: This patent is subject to a terminal disclaimer.

[21] Appl. No.: 08/965,332

[22] Filed: Nov. 6, 1997

Related U.S. Application Data

[63] Continuation of application No. 08/690,909, Aug. 1, 1996, abandoned, which is a continuation of application No. 08/327,979, Oct. 24, 1994, Pat. No. 5,553,486, which is a continuation-in-part of application No. 08/131,405, Oct. 3, 1993, abandoned.

[51] Int. Cl.[7] .............................. G01B 5/28; G01N 3/42
[52] U.S. Cl. .................. 73/105; 73/862.626; 361/283.2; 361/283.3; 361/283.4
[58] Field of Search .............................. 73/105, 862.626, 73/862.628, 718, 720, 724; 361/271, 280, 281, 283.1, 283.2, 283.3, 283.4

[56] References Cited

U.S. PATENT DOCUMENTS

| | | | |
|---|---|---|---|
| 3,307,407 | 3/1967 | Berg et al. | 73/432 |
| 3,314,493 | 4/1967 | Kennedy | 177/210 |
| 3,418,546 | 12/1968 | Beavers et al. | 317/246 |
| 4,040,118 | 8/1977 | Johnston | 361/283 |
| 4,089,036 | 5/1978 | Geronime | 361/283 |
| 4,196,632 | 4/1980 | Sikorra | 73/718 |
| 4,237,989 | 12/1980 | Lewis | 177/210 |
| 4,294,321 | 10/1981 | Wittlinger et al. | 177/210 FP |
| 4,310,806 | 1/1982 | Ogasawara | 331/40 |
| 4,479,392 | 10/1984 | Froeb et al. | 73/862.68 |
| 4,523,473 | 6/1985 | Chamuel | 73/643 |
| 4,523,474 | 6/1985 | Browne et al. | 73/724 |

(List continued on next page.)

FOREIGN PATENT DOCUMENTS

| | | |
|---|---|---|
| 1-195338 | 8/1989 | Japan . |
| 2-231546 | 9/1990 | Japan . |
| 2 189 607 | 10/1987 | United Kingdom . |
| WO 88/00691 | 1/1988 | WIPO . |

OTHER PUBLICATIONS

Wickramasinghe, "Scanned–Probe Microscopes", *Scientific American*, Oct., 1989, pp. 98–105.

Grigg, et al., "Tip–sample forces in scanning probe microscopy in air and vacuum", *J. Vac. Sci. Technol. A*, vol. 10, No. 4, Jul./Aug., 1992, pp. 680–683.

Heerens, "Application of capacitance techniques in sensor design", *J. Phys. E. Sci. Instrum.*, vol. 19, 1986, pp. 897–906.

Nishibori et al., "Ultra–Microhardness of Vacuum–Deposited Films in Ultra–Microhardness Tester", *Thin Solid Films*, vol. 48, 1978, pp. 325–331.

(List continued on next page.)

*Primary Examiner*—Daniel S. Larkin
*Attorney, Agent, or Firm*—Nawrocki, Rooney & Sivertson, P.A.

[57] ABSTRACT

A force, weight or position sensor unit and sensor element incorporated into an apparatus for microindentation hardness testing and surface imaging which allows immediate imaging of the surface subsequent to hardness testing. The sensor uses a multi-capacitor system having drive and pick-up plates mounted on an appropriate suspension system to provide the desired relative motion when a force is applied to the pick-up plate. The output signal is run through a buffer amplifier and synchronously demodulated to produce a signal proportional to force or displacement. The sensor element is mounted on a scanning tunneling microscope base and a sample mounted on the sensor. The force sensor is used for both measuring the applied force during microindentation or micro hardness testing and for imaging before and after the testing to achieve an atomic force microscope type image of the surface topography before and after indentation testing.

24 Claims, 6 Drawing Sheets

U.S. PATENT DOCUMENTS

| | | | |
|---|---|---|---|
| 4,550,617 | 11/1985 | Fraignier et al. | 73/862.04 |
| 4,685,678 | 8/1987 | Frederiksen | 273/148 |
| 4,694,687 | 9/1987 | Bonin et al. | 73/116 |
| 4,699,000 | 10/1987 | Lashmore et al. | 73/81 |
| 4,750,082 | 6/1988 | Gerety | 361/283 |
| 4,820,051 | 4/1989 | Yanagisawa et al. | 356/378 |
| 4,848,141 | 7/1989 | Oliver et al. | 73/81 |
| 4,922,444 | 5/1990 | Baba | 364/566 |
| 4,970,374 | 11/1990 | Ueda et al. | 219/518 |
| 5,006,952 | 4/1991 | Thomas | 361/283 |
| 5,065,103 | 11/1991 | Slinkman et al. | 324/458 |
| 5,083,091 | 1/1992 | Frick et al. | 324/678 |
| 5,092,174 | 3/1992 | Reidemeister et al. | 73/517 |
| 5,115,291 | 5/1992 | Stokes | 357/26 |
| 5,128,671 | 7/1992 | Thomas, Jr. | 341/20 |
| 5,134,886 | 8/1992 | Ball | 73/718 |
| 5,174,159 | 12/1992 | Jacobsen et al. | 73/767 |
| 5,193,383 | 3/1993 | Burnham et al. | 73/105 |
| 5,255,562 | 10/1993 | Yamamoto et al. | 73/160 |
| 5,305,633 | 4/1994 | Weissenbacher et al. | 73/82 |
| 5,359,879 | 11/1994 | Oliver et al. | 73/7 |
| 5,381,300 | 1/1995 | Thomas et al. | 361/280 |
| 5,383,364 | 1/1995 | Takahashi et al. | 73/517 R |
| 5,406,832 | 4/1995 | Gamble et al. | 73/105 |
| 5,412,327 | 5/1995 | Meinen | 324/686 |
| 5,421,213 | 6/1995 | Okada | 73/862.04 |
| 5,424,650 | 6/1995 | Frick | 324/688 |
| 5,437,196 | 8/1995 | Okada | 73/862 |
| 5,492,020 | 2/1996 | Okada | 73/862 |
| 5,553,486 | 9/1996 | Bonin | 73/105 |
| 5,576,483 | 11/1996 | Bonin | 73/105 |

OTHER PUBLICATIONS

Tsukamoto et al., "Mechanical Properties of Thin Films measurements of Ultramicroindentation Hardness Young's Modulus and Internal Stress".

Yanagisawa et al., "An Ultramicro Indentation Hardness Tester and Its Application to Thin Films", *Lubrication Engineering*, vol. 45, Jan., 1987, pp. 52–56.

Newey et al., "An ultra–low–load penetration hardness tester", *J. Phys. E. Sci. Instrum.*, vol. 15, 1982, pp. 119–122.

Wierenga et al., "Ultramicroindentation apparatus for the mechanical characterization of thin films", *J. Appl. Phys.*, vol. 55, No. 12, Jun. 15, 1984, pp. 42244–42247.

Wierenga et al., "Ultramicrohardness Experiments on Vapour–Deposited Films of Pure Metals and Alloys", *Thin Solid Films*, vol. 119, 1984, pp. 375–382.

Burnham et al., "Measuring the nanomechanical properties and surface forces of materials using an atomic force microscope", *J. Vac. Sci. Technol. A*, vol. 7, No. 4, Jul./Aug., 1989, pp. 2906–2913.

Oliver et al., "Thin Film Characterization Using a Mechanical Properties Microprobe", *Thin Solid Films*, vol. 153, 1987, pp. 185–196.

Wu, "Microscratch and load relaxation tests for ultra–thin films", *J. Mater. Res.*, vol. C, No. 2, Feb., 1991, pp. 407–426.

Holman et al., "Using capacitive sensors for in situ calibration of displacements in a piezo–driven translation stage of an STM", *Sensors and Actuators A*, vol. 36, 1993, pp. 37–42.

Weihs et al., "Mechanical deflection of cantilever microbeams: A new technique for testing the mechanical properties of thin films", *J. Mater. Res.*, vol. 3, No. 5, Sep./Oct. 1988, pp. 931–942.

APPARATUS FOR MICROINDENTATION HARDNESS TESTING AND SURFACE IMAGING INCORPORATING A MULTI-PLATE CAPACITOR SYSTEM

RELATED APPLICATION

This application is a continuation of U.S. application Ser. No. 08/690,909, filed Aug. 1, 1996, now abandoned, which is a continuation of U.S. application Ser. No. 08/327,979, filed Oct. 24, 1994, now U.S. Pat. No. 5,553,486, which is a continuation-in-part of U.S. application Ser. No. 08/131,405, filed Oct. 3, 1993, now abandoned.

TECHNICAL FIELD

The present invention relates to apparatus for microindentation hardness testing and subsequent surface imaging of the results with high resolution capability. More particularly, it is directed to such devices incorporating a sensor, including a multi-plate capacitor system.

BACKGROUND OF THE INVENTION

Many applications for precise measurement of force, weight, and relative position are known in the art. For example, machine shop tools for precisely indicating or fabricating holes, channels or other surface features relative to one another require accurate position or displacement measurement. Accurate measurement of displacement or position on small parts, such as those used in the manufacture of electronic components is particularly important.

Measurement of force or weight accurately at minute quantities, along with instruments to accomplish such measurements are well known. Strain gauge transducers are one industry recognized instrument for such measurements. These instruments can be used in laboratory analysis, such as micro hardness testing of samples. Furthermore, laboratory scales for measuring constituent components in minute quantities with high resolution are well known in chemical, biological, drug and medical fields.

A known limitation to resolution in strain gauge transducers is the signal to noise ratio of the instrument. Strain gauge transducers have an output of only a few millivolts. It is recognized that the minimal possible noise level for the strain gauge transducer is set by the thermal noise on the strain gauge resistive element. For example, the calculated noise for a commercial strain gauge sensor with 350 Ohm resistance is 2.4 nV at 1 Hz bandwidth.

In more recent years, the development of scanned-probe microscopes has created a need for higher resolution measurement of force and position at minute levels. As disclosed by Wickramasinghe in "Scanned-Probe Microscopes", *Scientific American*, October, 1989, pp. 98–105, scanned-probe microscopes allow an examination of a surface at very close range with a probe that may be just a single atom across, and resolve features and properties on a scale that eludes other microscopes.

The disclosure of Wickramasinghe, which is incorporated herein by reference, discloses two types of scanned-probe microscopes. The first type is a scanning tunneling microscope, while the second is an atomic force microscope.

In the atomic force microscope, a scanned-probe device moves a minute tip, such as an atomically sharp diamond mounted on a metal foil over a specimen in a raster pattern. The instrument records contours of force, the repulsion generated by the overlap of the electron cloud at the tip with the electron clouds of surface atoms. In effect, the tip, like the stylus of a phonograph, reads the surface. The foil acts as a spring, keeping the tip pressed against the surface as it is jostled up and down by the atomic topography.

A scanning tunneling microscope senses atomic-scale topography by means of electrons that tunnel across the gap between a probe and the surface. Piezoelectric ceramics, which change size slightly in response to changes in applied voltage, maneuver the tungsten probe of a scanning tunneling microscope in three dimensions. A voltage is applied to the tip, and is moved toward the surface, which must be conducting or semiconducting, until a tunneling current starts to flow. The tip is then scanned back and forth in a raster pattern. The tunneling current tends to vary with the topography. A feedback mechanism responds by moving the tip up and down, following the surface relief. The tip's movements are translated into an image of the surface.

With scanning tunneling microscopy, it is recognized that measurement of surface topography would be incorrect if the tip distance from the surface is not maintained. Thus, a measurement of the force applied by the tip on the sample throughout the measurement cycle would serve to confirm that such distance is maintained, and provide a cross-check for the accuracy of the topographic measurement.

As previously stated, instruments such as strain gauge transducers can be used for micro hardness testing of samples while scanning tunneling microscopes and atomic force microscopes are recognized methods for measuring or imaging surface topography. There would be a significant advantage when making microindentation hardness tests if it were possible to immediately image the results with high resolution capability. Presently known tips and control mechanisms for scanning tunneling microscopes and atomic force microscopes have heretofore prevented these instruments from being capable of both measuring surface topography and conducting microindentation hardness tests.

The tungsten scanning tunneling microscope tips generally used on these instruments are very slender and tend to bend into a fish hook shape at rather low indentation loads so that imaging after indentation is somewhat suspect. The atomic force microscope tips, although harder than the tungsten scanning tunneling microscope tips, are mounted on a delicate cantilever which is easily broken off. This limits the amount of force that can be applied with the atomic force microscope to much less than is needed for most indentations.

An alternative approach is to build a scanning tunneling or atomic force microscope with a built in scanning electron microscope which gives the imaging capability after indentation but at a considerable expense in equipment cost and added time. Also, the scanning electron microscope only works under vacuum so that observation of moist samples, such as biological specimens is not possible.

In studying mechanical properties of materials on the microscopic scale, indentation and scratch testing are two frequently used techniques. Indentation testing, where a diamond tip is forced into the material being tested is commonly used for determining hardness, and is beginning to be used to determine elastic modulus. The scratch test is used to determine (among other things) the adhesion of a film or coating deposited on a substrate. This is done by dragging the diamond tip across the sample surface under increasing load until a critical load is reached at which time some kind of delamination or failure occurs.

Normally the indentation or scratch is performed on one machine designed for that purpose, and the results are analyzed by using a microscope to determine the indent size or area of delamination. For feature sizes of a few micrometers or greater this is usually done with an optical microscope.

For features of less than a few micrometers, as are becoming increasingly important with the continued miniaturization of semiconductors and decreased thickness of protective coatings, such as used on magnetic storage disks, the area would normally be determined by scanning electron microscope imaging. This involves significant work in sample preparation, especially for samples that are electrical insulators and need to be gold or carbon coated before imaging on the scanning electron microscope. Also, just finding the tiny indent or scratch is not trivial. For the smallest indents and scratches, the atomic level resolution of the scanning tunneling microscope or atomic force microscope may be required to accurately resolve the scratch widths and areas of delamination. Researchers have reported spending up to eight hours locating an indent on the atomic force microscope after producing it on a separate microindentor.

Another source of uncertainty is plastic flow or relaxation that may take place with certain samples. If this occurs over time periods of an hour or less, an indent produced by a separate indentor may disappear before it can be inspected on a microscope. Indents made in the 50 Angstrom range, have sometimes indicated plastic deformations that could not be seen with the scanning electron microscope or atomic force microscope imaging. Possible explanations include mechanical hysterisis in the indentor causing it to indicate plastic deformation that was not actually present. It is also possible that there actually was an indent present that the researcher was not able to locate. A third possibility is that the sample exhibited a relaxation effect where the indent was actually present, but disappeared by some plastic flow phenomena before the sample could be observed in the microscope.

There would obviously be a significant advantage when making microindentation hardness and scratch tests if it were possible to immediately image the results with high resolution capability. Such capability would both reduce time and cost of the measurements and reduce uncertainties about the results.

Bonin et al. (U.S. Pat. No. 4,694,687) discloses a vehicle performance analyzer which incorporates a capacitive accelerometer for detecting changes in G-forces and for producing a digital count value proportional to such changes. The sensor includes a capacitive transducer comprising a pair of spaced-apart parallel plates disposed on opposite sides of a beam-supported moveable plate, which responds to changes in acceleration of forces. Bonin et al. discloses, in FIG. 3, that the beam-supported moveable plate is sealed from access between the spaced-apart parallel plates. Thus, although not physically accessible, the moveable plate will yield and be displaced when subjected to G-forces during acceleration when mounted perpendicular to such force. Bonin et al. (U.S. Pat. No. 4,694,687) is hereby incorporated by reference.

SUMMARY OF THE INVENTION

The present invention provides a force, weight or position sensor unit and sensor element in a first embodiment. In a second embodiment, the sensor element of the first embodiment is incorporated into an apparatus for microindentation hardness testing and surface imaging which allows immediate imaging of the surface subsequent to hardness testing.

First, turning to the first embodiment of the present invention, a force, weight or position sensor unit and sensor element is provided. The output from the sensor may be converted to a DC signal proportional to the weight, force or relative position of the measured sample. This conversion may be accomplished as generally disclosed by Bonin et al. in U.S. Pat. No. 4,694,687, for example.

In a preferred embodiment, the sensor uses a multi-capacitor system having drive and pick-up plates mounted on an appropriate suspension system to provide the desired relative motion when a force is applied to the pick-up plate. The drive plates may be driven with an AC carrier signal in the order of 50 KHz, with the driving signals being 180 degrees out of phase with each other.

The output signal is run through a buffer amplifier of very high input impedance (100 M Ohm–0.3 pF, for example), and then synchronously demodulated to produce a DC signal proportional to force or displacement. The output is positive for one direction of displacement, and negative for the opposite direction.

A sensor element in accordance with the present invention includes a pair of capacitive transducers, each transducer including a separate drive plate and a shared pick-up plate. One of the pair of drive plates includes a hole therethrough centrally disposed on the drive plate. The pick-up plate is positioned between the pair of drive plates and spaced from each drive plate by an insulating spacer. Thus, the drive plates, in a preferred embodiment, generally include spaced opposing conductive surfaces when the pick-up plate is mounted therebetween. The pick-up plate can be generally a conductive central plate suspended by a spring means between the drive plates, wherein the central plate is capable of deflection between the conductive surfaces of each of the drive plates.

The sensor element includes means for transmitting force from a point remote from the central plate to the central plate. The means can include a sample holder which is attached to the pick-up plate so that it moves in unison with such plate. Alternatively, any rod or member passed through the hole in one drive plate and in contact with the central plate may transmit force to the pickup plate. The output is actually proportional to the pick-up plate position, but can easily be calibrated to represent force since the sensor may be constructed to have a linear force versus displacement relationship.

In a preferred embodiment, the sample holder is a pedestal having a stem portion which passes through the centrally disposed hole in one drive plate and remains in contact with the surface of the conductive central plate of the pick-up plate. Contact with the central plate is approximately at its center point. Thus, the pedestal transmits a force applied to the pedestal to the central plate with resulting deflection of the central plate. A diaphragm seal can be included to prevent dust or other contaminants from entering through the space between the pedestal stem and hole in the drive plate.

The disclosed force sensor is particularly useful in conjunction with scanned-probed microscopes, such as a scanning tunneling microscope or an atomic force microscope. It is, however, recognized that the sensor may be utilized in any application for measuring weight, force or displacement that requires high resolution of minute measurements. The force sensor of the present invention has a resolution of over 100,000 to 1. The sensor can be of a size ½" square and ⅛" thick, which allows it to be mounted on the sample holder region of an existing scanned-probe microscope. The sample to be subjected to microscopy can then be mounted on top of the sensor. This gives a direct readout of the force applied to the sample by the microscope tip.

The signal to noise ratio of the sensors of the present invention are much higher than those calculated for existing strain gauge transducers. As previously stated, the minimum possible noise level for a strain gauge transducer is set by the thermal noise of the strain gauge element. In contrast, the capacitive sensor of the present invention has a noise level controlled by the impedance of the sensor. This allows for a signal to noise ratio of a capacitive transducer of the present invention that exceeds that of a strain gauge by more than 10 times. This can be increased even further by increasing the carrier signal beyond 50 KHz. The useable resolution is limited by thermal stability, but it is believed that the thermal stability can be improved with use of more stable materials, and that automatic correction of base line drift is also possible.

The sensor element of the present invention comprises first and second, serially connected variable capacitors which may be readily fabricated using conventional printed circuit etching techniques. More specifically, the sensor comprises a stacked configuration of five substrates.

The two outermost substrates, or first and fifth substrates, have a metalized surface on each side thereof. A portion of the metal surface on the inner side of the outer most plates each comprise the first plates (drive plates) of a different variable capacitor. The first substrate further includes a hole or passage therethrough for receiving means for transmitting force to the pickup plate (from a sample holder, for example) without contacting or being frictionally restrained from movement therethrough. The pick-up plate is described more fully below. The fifth substrate further includes an area directly opposite and conforming to the size of the hole or passage in the first substrate in which the metalized surface is etched therefrom on the inner surface. This is done to maintain linearity of response of the sensor. The metalized surfaces of the outer side of the first and fifth substrates act as shields, in known manner.

The first and fifth or outer substrates each abut the second and fourth substrates, respectively, which comprise insulating substrates or frame members having an open central portion at least as large as a central plate of the third substrate described below.

The third substrate is sandwiched between these two insulating frame members. A portion of the third substrate comprises a common second plate or pick-up plate for the pair of variable capacitors defined by the first and fifth substrates. The third substrate includes a planar central plate which is suspended by spring-like members. In preferred embodiments, the spring-like members include four relatively thin L-shaped springs. The metal mass is thus displaceable within the frame openings when the five substrates are sandwiched together.

The means for transmitting force to the central plate, for example sample holder or pedestal, passes through the first and second substrate without contact, while abutting, contacting or attaching to the suspended metal mass proximate it center. In this way, forces applied to the sample holder or pedestal are translated to displacement of the suspended metal mass.

Electrical connections to various layers of substrates in the construction outlined above can be made by conductive pins inserted through metalized holes made using conventional plate through hole techniques common to multi-layered printed circuit assemblies.

Means for applying an alternating current carrier signal to the pair of drive plates is provided. An alternating current signal from a high frequency oscillator is impressed across the terminals associated with the first and fifth substrates or two outer most stationary plates of the transducer and the central displaceable plate (pick-up plate) provides an output. As such, a push-pull signal proportional to the amount of deflection of the central moveable plate is developed and subsequently amplified, and then synchronously demodulated by means for monitoring an output signal. A DC voltage signal which is proportional to force, weight or displacement can be produced.

In a second embodiment, the above described sensor can also be utilized as a device for measuring ultra-microhardness of samples with the capability of simultaneous or immediately subsequent scanning tunneling microscopy or atomic force microscopy imaging. It has been found that sensors of the present invention can readily provide a full scale range of 3 grams with resolution to 30 micrograms.

When the sensor of the present invention is utilized in an apparatus for microindentation and imaging, the sensor is utilized to generate the deflection signal which is presently obtained in atomic force microscopy from the photo sensor output of a laser reflected off the cantilever. Further, with this second embodiment, the sample is mounted on the force sensor, and a suitable indentor tip or other hard, sharp tip is mounted on a scanning tunneling microscope piezo actuator. It has been found not necessary for either the indentor tip or sample to be conductive, as the force output from the sensor is sent back to the control unit, causing the system to operate much like a standard atomic force microscope.

The sample can be imaged by specifying a contact force at a suitably low value to not affect the sample. After imaging, the controller can be used to force the tip into the sample and produce the indent, with the force sensor providing a reading of the applied load during the indenting process. The scanned probe microscope piezo can be used to force the tip into the sample to form the indent. The sample can then be reimaged with the same tip so that the results of the indent can be seen in minutes rather than hours, as would be the case when using a separate indenting apparatus.

These and various other advantages and features of novelty which characterize the present invention are pointed out with particularity in the claims annexed hereto and forming a part hereof. However, for a better understanding of the invention, its advantages, and the object obtained by its use, reference should be made to the drawing which forms a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

Detailed embodiments of the present invention are described herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention includes generally two embodiments. The first embodiment directed to a force or position indicating device or sensor and the second embodiment directed to an apparatus for microindentation hardness testing and subsequent surface imaging of the results with high resolution capacity. The second embodiment utilizes, in preferred designs, the sensor element of the first embodiment. The force or position indicating device or sensor is thus described first. The apparatus for microhardness testing and subsequent surface imaging utilizing the sensor is then described, recognizing that the disclosure with regard to the force sensor alone is equally applicable to the test apparatus utilizing such sensor.

The force (including weight) or position indicating device or sensor of the present invention generally has three components. The first component is a sensor element, which is a multi-plate capacitor system. A second component is means for inputting an AC carrier signal, while the third component is means for monitoring the sensor element output, preferably converting the output from the sensor to a DC signal proportional to force, weight or displacement.

Figure 1:
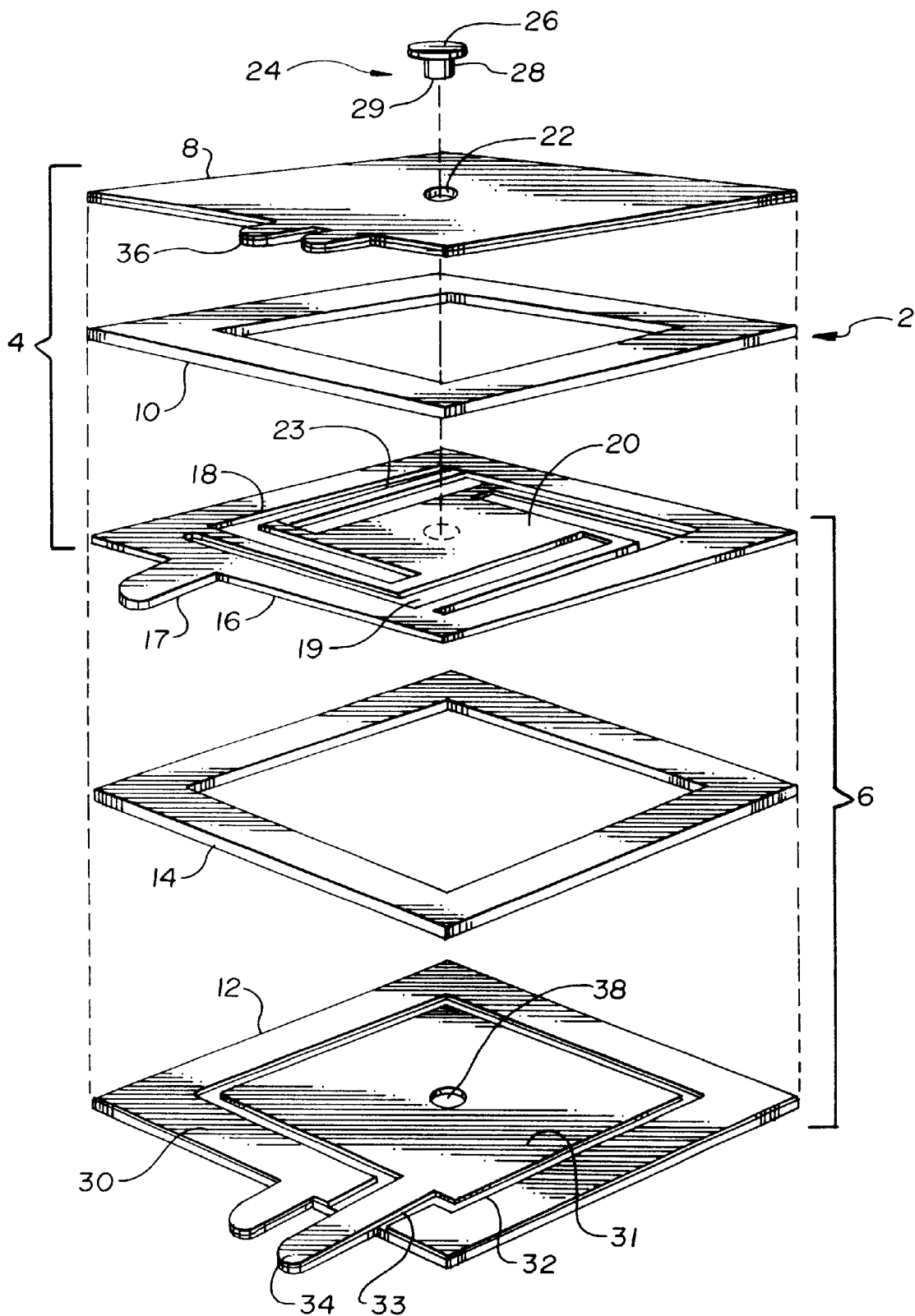
FIG. 1 depicts an exploded view of a capacitative sensor element in accordance with the present invention.

Referring now to FIG. 1, an exploded view of the components of the sensor element 2 of the present invention, is depicted. Functionally, the sensor element comprises two transducers 4, 6, which function as two variable capacitors connected in series and forming a capacitive voltage divider. The overall sensor element 2 includes five substrate layers 8, 10, 16, 14, 12 sandwiched together to form the transducers. The sensor element 2 can be fabricated using well-known printed circuit etching technology.

The first substrate layer 8 and the fifth substrate layer 12 include the drive plates or fixed plates of the transducers and are driven with a carrier signal. The carrier signal can be an AC signal on the order of 50 KHz, with the signal to these outer most substrate layers 8, 12, being 180 degrees out of phase with each other.

The outer exposed surfaces of first substrate 8 and fifth substrate 12 are covered with metalization, for example, copper. This metal layer functions as a shield against EMI noise. On the inner surface of first substrate 8 and fifth substrate 12, a metalized pattern 30 is provided. This metalized pattern forms the drive plate on each substrate. The metalized pattern on the interior surface of the first substrate 8 generally corresponds to that on the fifth substrate 12. As depicted in FIG. 1, the metalized pattern 30 or drive plate on the inside of the fifth substrate 12 can include a generally rectangular frame pattern 31. Extending around the periphery of the substrate metalized pattern 31 is a channel defining an unmetalized opening 32. Centrally disposed in this unmetalized opening 32 is the rectangular metalized pattern 31 of conductive material, having a conductive lead 33 leading to a conductive terminal portion 34.

The metalization on the inside surface of the first substrate 8 is similar to that of the inside surface of fifth substrate 12 with two exceptions. The first difference is that the terminal portions of each substrate 34, 36 are offset from one another, rather than being vertically aligned when the sensor element 2 is assembled. The second difference is the provision of a through hole 22 centrally disposed through the thickness of the first substrate 8. The through hole 22 is disposed centrally for receiving a sample holder 24 or other means for transmitting force therethrough, which is described in further detail below.

The inside surface of the fifth substrate 12 includes a demetalized or etched portion 38 which corresponds to the through hole 22. The provision of the demetalized or etched portion 38 generally corresponding to the through hole 22 provides for the rectangular metalized pattern 30 of conductive material on each of the first substrate 8 and fifth substrate 12 inside layers to be mirror images of one another. This provision is necessary to provide a linear response from the pair of capacitive transducers 4, 6.

The outer layers of the sensor element 2 or first substrate 8 and fifth substrate 12 can be manufactured from standard circuit board materials, such as $\frac{1}{16}$" glass epoxy with copper on both sides. In order to reduce labor requirements, a large number of the outer layer substrates may be manufactured at one time. For example, a 6" sheet of material may be utilized to manufacture about 100 substrate layers of $\frac{1}{2}$" square dimensions. The pattern for the metalized portion 30 of the first substrate 8 and fifth substrate 12 may be first etched in the copper. The substrate may be routed around the individual devices within a large sheet of material, leaving only thin tabs of materials to hold them together. These tabs allow the devices to be snapped apart after assembly.

The second substrate layer 10 and the fourth substrate layer 14 comprise spacer layers. As depicted in the figure, these layers 10, 14 may be of generally rectangular shape and have a generally rectangular opening formed centrally therein, with the opening extending completely through the substrate. The spacer layers, second substrate 10 and fourth substrate 14, must be insulators or covered with an insulating coating. The opening through the insulators 10, 14 is equal to or greater than the dimensions of a central plate 20 on a third substrate 16 described below, and an associated appropriate suspension system 18, also described below.

The second substrate 10 and fourth substrate 14 can be manufactured from etched metal with an insulating coating on both sides. This insulating coating could be an epoxy, or other organic coating such as those used on enameled magnet wire, but it is believed that best results are achieved by using aluminum for the spacer and anodizing it to form an insulating coating of aluminum oxide.

It is believed that the insulating spacers, second substrate layer 10 and fourth substrate layer 14, can be etched first and then anodized, or anodized first and then etched, depending upon the type of photoresist chemicals used. A preferred method is to use aluminum sheet stock purchased with a thin (0.00012") anodized layer on both sides. This anodized layer provides good adhesion with the positive type liquid photoresist which can be used to fabricate the other layers of the sensor element 2. With bare aluminum, the resist tends to peel away at the edges being etched making it hard to maintain desired dimensions.

After etching, the photoresist and original anodizing are removed and the parts are anodized to the desired insulation thickness. Although it is believed 0.0005" or less of an anodized thickness layer will provide the required electrical isolation, it is desirable to make the thickness as great as possible to minimize the capacitance between the outer layer shields, first substrate layer 8 and fifth substrate layer 12, and a center plate, third substrate layer 16, described below.

The third substrate layer 16 is sandwiched between the insulating layers, second substrate layer 10 and fourth substrate layer 14. The third substrate layer 16 includes the pick-up plate which is common to the pair of transducers 4, 6. A central plate 20 is mounted on an appropriate suspension system 18 to provide for desired relative motion of the central plate 20 or pick-up plate on third substrate layer 16. The third or central substrate layer 16 can be an etched metal layer supported by a suspension system 18 defined by a pattern of slits 19. The central plate 20 is thus a solid portion or mass suspended by the surrounding framework of a suspension system 18. The third substrate layer further includes a terminal 17 for electrical connection. A preferred metal for use as a central plate is a beryllium-copper alloy.

Although a pattern of four L-shaped slits 19 are depicted in the figure, it is believed that other patterns may be utilized to provide the same type of spring supporting structure for central plate 20. Further, it is recognized that varying effective spring constants may be achieved for the centrally supported mass or central plate 20 by altering the thickness of the materials of this substrate and the size of the spring elements. Thus, the overall range of travel per unit force exerted on the central plate 20 of the third substrate layer 16 may be varied by design. Thus, sensors of varying overall range may be manufactured.

When the five substrate layers 8, 10, 16, 14, and 12 are assembled together, the central plate 20 of the third substrate layer 16 is centrally disposed within the openings formed in the insulating substrates, second substrate layer 10 and fourth substrate layer 14, and thus, the central plate 20 is free to deflect relative to the first substrate layer 8 and fifth substrate layer 12.

The layers may be assembled together by hand, holding them together with pins inserted around the entire perimeter of the substrates and soldered to the outside layers. When assembled, selected electrical connections between the various internal layers or substrates can readily be provided as disclosed by Bonin et al. in U.S. Pat. No. 4,694,687.

Means for transmitting force 24 from a point remote from the central plate 20 to the central plate 20 are provided. This means can include a sample holder 24, which functions to transmit the force created by the weight of a sample to the central plate 20 of the third substrate layer 16. In a preferred embodiment, the sample holder 24 is a pedestal which includes a sample holding surface 26 and a stem portion 28. The stem portion 28 extends through the through hole 22 in the first substrate layer 8 and through the opening in the second substrate layer 10. The bottom surface 29 of the stem portion 28 contacts the upper surface of the central plate 20 at a central point 23 when the sensor is assembled. The space between the stem portion 28 and wall of the through hole 22 is preferably sealed from contamination by a diaphragm seal or other sealing means which prevents entry of dirt while not impeding movement of the pedestal or other means for transmitting force 24.

Thus, functionally, the weight or force exerted by a sample or other means on the sample holding surface 26 of the sample holder 24 is transmitted to the central plate 20 of the third substrate layer 16 and results in deflection of the central plate 20 commensurate with the force exerted on the surface of the sample holder 24. Thus, the central plate 20, under force, moves closer toward or further away from one or the other of the outer most substrates, first substrate layer 8 and fifth substrate layer 12. Of course, the sample holder 24 may be directly connected to a moving, or force imparting, element without positioning a "load" on the surface 26. Indeed, the surface 26 may be replaced by a connector adapted for this purpose.

Means for providing a carrier signal to the outer most plates or first substrate layer 8 and fifth substrate layer 12 are provided. This signal can be an AC signal. Such means may include an oscillator which produces a 50 KHz alternating current signal. The signal to each outer most plate is preferably 180 degrees out of phase with the signal provided to the other outer most plate.

Means are also provided for reading the output from the sensor element 2, and converting the output to a signal proportional to force, weight or displacement of the central plate 20. The output signal is generally run through a buffer amplifier of very high input impedance (100 MOBM–0.3 pF), and then synchronously demodulated to produce a DC signal. The DC signal is proportional to the force, weight or displacement of the central plate 20. The output would be positive for one direction of displacement, and negative for the opposite direction. It is recognized that the sample holder 24 or means for transmitting force is attached or in contact with the central plate 20 to move in unison with such central plate 20. The output of the sensor 2 is actually proportional to the central plate 20 position, but can easily be calibrated to represent force (including weight) since the sensor has a linear force versus displacement relationship.

It is recognized that the sample holder 24 or means for transmitting force must be manufactured from an insulating material or covered with an insulating material. Further, the clearance between the inside diameter of through hole 22 and the outside diameter of stem portion 28 must be sufficient to avoid any frictional effects which may reduce the sensitivity of the sensor element 2.

The signal to noise ratio of the capacitive transducers of the present invention are much better than that of presently used metal strain gauge transducers. The minimum noise level of the strain gauge transducer is determined by the thermal noise of the strain gauge resistive element. This noise is proportional to the square root of the resistance. The output signal is proportional to the input signal, but is only a very small fraction of it. A typical value taken from a commercial scale strain gauge transducer is 175 Ohm resistance at full scale output of 5 millivolts.

The three-plate capacitive transducer of the present invention does not generate noise as a resistive transducer does, but the signal cannot be used without connecting it to an amplifier, and the amplifier must have a very high input resistance, so the amplifier will generate noise. The lower limit of this noise will be determined by the effective input impedance of the amplifier. Since the capacitive transducer is in parallel with the amplifier input impedance, and the amplifier input impedance is much larger than the impedance of the transducer (or the output will be very non-linear), the effective input impedance is equal to that of the transducer.

The impedance of the transducer is determined by the capacitance and operating frequency. Higher operating frequency gives lower transducer impedance ($X_c = 1/6.28 \, FC$).

The capacitance is about 10 pF for the ½" square device with 0.005" spacing between plates. The operating frequency can be any convenient value, limited only by the frequency response of the amplifier and associated circuitry. The full scale output signal of the transducer is equal to the input voltage, which will be conservatively taken as 10 volts. The full scale output of the capacitive transducer is 10V, which is 2,000 times greater than the strain gauge transducer (5 mV). The impedance, and therefore the noise generated, is greater with the capacitive transducer (except at very high frequencies which would require rather expensive components), but due to the much higher inherent output level, the signal to noise ratio of the capacitive transducer is significantly better.

The following table shows the relationship of signal to noise ratio for the two transducers.

TABLE 1

Fop = operating frequency of capacitive transducer
C = capacitance of transducer = 10 pF
Xc = impedance of transducer = 1/(6.28 × Fop × C)
R = resistance of strain gauge = 175 Ohm
Since noise is proportional to the square root of R or Xc, the ratio of capacitive transducer noise to strain gauge noise is the square root of (Xc/R), and the factor of improvement of SNR of capacitive vs strain gauge is 2000 divided by the square root of (Xc/R).

| Fop | Xc/R | square root Xc/R | 2000/sq root (Xc/R) |
|---|---|---|---|
| 10 KHz | 11,400 | 107 | 19 |
| 100 KHz | 1,140 | 34 | 59 |
| 1 MHz | 114 | 11 | 190 |
| 10 MHz | 11.4 | 3.4 | 590 |
| 100 MHz | 1.14 | 1.1 | 1900 Capacitive transducer SNR is better than strain gauge by factor in above column. |

As is readily apparent from the above table, the capacitive transducer sensor of the present invention is far superior to strain gauges on the basis of electronic noise.

Since the output of the capacitive transducer or sensor element 2 is proportional to the displacement of the center mass portion 20 or electrode, it is recognized that a device for use as a scale or as a measure of displacement may be manufactured. It is first necessary to choose an appropriate stiffness for the suspension system 18 supporting the central plate 20 so that the sample holder 24 or means for transmitting force is forced reliably against the surface to be measured without exerting excessive force that would deflect the object and change its actual position. Secondly, it is recognized that the insulating spacers, second substrate layer 10 and fourth substrate layer 14, may be manufactured of different thicknesses to offset the center plate sufficiently. This would alter the operational range of the device. With resolution of one part in 100,000, it is believed that such sensors can resolve displacements down to 0.1 microinches or just 25 Angstroms or better.

Figure 2:
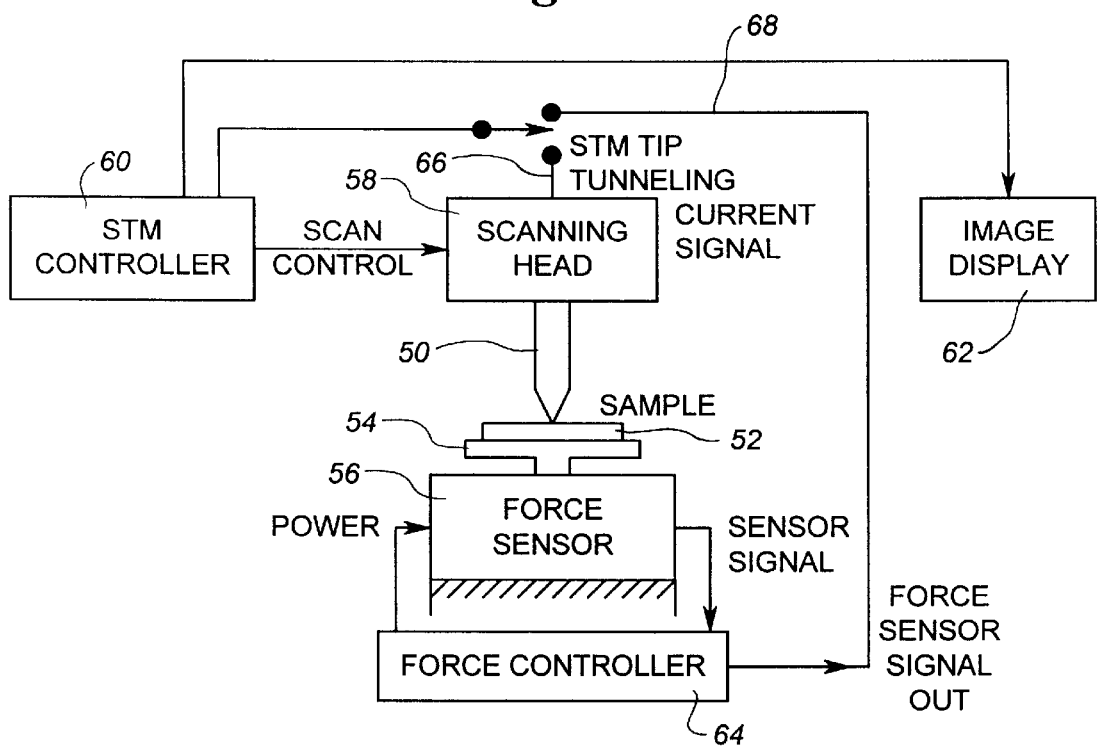
FIG. 2 is a schematic representation of an apparatus for hardness testing and surface imaging incorporating the sensor of the present invention.

Now referring to FIG. 2, a schematic representation of an apparatus for hardness testing and surface imaging incorporating the above-described sensor of the present invention is depicted. With this second embodiment, it is possible to conduct a scan of the surface topography of a sample, followed immediately by microindentation testing, followed by a second imaging of the surface topography all on the same instrument. Generally, the schematic in FIG. 2 depicts a commercial scanning tunneling microscope, such as the Nanoscope III, available from Digital Instruments, which has been modified to conduct the in-situ high resolution imaging and microindentation testing on a single instrument.

As previously stated, scanning tunneling microscopes are commercially known. As disclosed by Wickramasinghe in "Scan-Probe Microscopes", Scientific American, October, 1989, pp. 98–105, which is incorporated herein by reference, scanning tunneling microscopes include several standard components which are depicted in FIG. 2.

With a scanning tunneling microscope, a sample 52 is placed on a sample platform 54 for analysis. The scanning tunneling microscope senses atomic-scale topography by means of electrons that tunnel across the gap between a probe 50 and the surface of the sample 52. A scanning head 58, (a piezo actuated head in the illustrated embodiment) has the probe mounted thereon. In other embodiments, the scanning head 58 may include a 3-D piezo actuator. The scanning head 58 is utilized to move the probe in three directions in response to changes in applied voltage. Piezoelectric ceramics are generally utilized because they change size slightly in response to such changes in voltage, and thus, maneuver the probe in three dimensions. The voltage applied to the scanning head 58 is controlled by the scanning tunneling microscope controller 60.

In use, voltage is applied to the tip of the probe 50 and it is moved toward the surface of the sample 52, which must be conducting or semiconducting, until a tunneling current starts to flow. The tip of the probe 50 is then scanned back and forth in a raster pattern by varying the voltage to the piezoelectric ceramics which control horizontal motion. The tunneling current tends to vary with the topography of the sample, and therefore, a current output signal 66, which provides a feedback mechanism, and which monitors such tunneling voltage, feeds such signal to the scanning tunneling microscope controller 60. The controller 60 adjusts the output to the scanning head 58 which responds by moving the tip of the probe 50 up and down, following the surface relief. The probe's 50 movements are translated into an image of the surface and displayed on an image display 62.

With scanning tunneling microscopy, the probe 50 is generally made from tungsten with a tip so fine that it may consist of only a single atom and measures as little as 0.2 nanometers in width.

The apparatus of Applicant's present invention for microindentation with subsequent surface imaging utilizes the above-described scanning tunneling microscope with several modifications. A force sensor 56, as described in the first embodiment, is mounted on the scanning tunneling microscope base in place of the standard sample holder. The sample 52 is then mounted on the sample platform 54. A force controller 64 is operatively connected to the force sensor 56 to monitor the output signal from the force sensor 56 and convert it to a signal proportional to the force being applied to the sample 52 on the platform 54 by the probe 50. The force controller 64 or the STM controller 60 can either separately or together perform functions of the means for providing a carrier signal 40 and the means for reading and converting the output 42 (shown in FIG. 1). The force controller or force sensor output signal may then be utilized to control the vertical position of the probe 50 or position along the Z axis by sending such signal through the scanning tunneling microscope controller 60 during surface imaging. Alternatively, the output from the force controller 64 can be monitored for measurement of force being applied during micro-indentation or micro hardness testing. These procedures are described below.

The scanning tunneling microscope described above is also modified by replacing the tungsten probe with a harder tip for microindentation testing. In a preferred embodiment, a diamond tip is used, such as blue diamond. It is not necessary for the tip to be conductive or a sample being tested to be conductive; however, it is recognized that conductive blue diamond scanning tunneling microscope tips are available. They can be used for scanning tunneling microscopy imaging of conductive samples, as well as testing with Applicant's apparatus.

In operation, the force sensor 56 of Applicant's second embodiment is used for both measuring the applied force during indentation or scratching and for imaging before and After testing. An atomic force microscope type image is first obtained from the scanning tunneling microscope by disconnecting the scanning tunneling microscope's tunneling current output signal 66 and substituting in its place the output signal 68 from the force sensor 56. The scanning tunneling microscopes scanning function can then be operated in a normal manner, with the force controller 64 output signal now controlling the Z axis piezoceramic to maintain a constant force between the probe 50 tip and the sample 52, rather than a constant tunneling current. Alternatively, a constant height image could be obtained where the probe 50 tip Z-position or vertical height is held constant, and the image is obtained directly from the force sensor 56 output signal from the force controller 64, which again passes through the scanning tunneling microscope controller 60 and results in a display of surface topography on the image display 62.

Once an image of the surface has been made using the above procedure, the controller can be used to force the tip into the sample and produce an indent, with the force sensor providing a reading of the applied load during the indenting process. The scanned probe microscope piezo can be used to force the tip into the sample to form the indent. In particular, in a preferred embodiment, the Z axis piezo can be manipulated to provide force to the tip which provides an indentation. After indentation, the sample can then be reimaged with the same tip so that the result of the indent can be seen in minutes, rather than hours, without the need for moving the sample or finding the point where the indentation was made in the sample. Further, because the first image, indentation, and second image are all made with the sample in a single position, it is assured that the first surface image and second surface image are of the same surface area and show the corresponding effect of the indentation step.

With the above-described system, both conducting and non-conducting samples can be imaged at high resolution before and after mechanical testing without disturbing the sample position so that there is no problem of trying to locate the test region as there is when using separate indenting and imaging equipment. It is also possible to compare side by side atomic force microscope images and scanning tunneling microscope images of the same sample surface by flipping a switch to change from atomic force microscope to scanning tunneling microscope. This is sometimes useful as the atomic force microscope signal is generally an accurate representation of the sample topography, while the scanning tunneling microscope signal may give some information about conductivity or electronic states of the surface.

Atomic force microscope images have been obtained using the sensor and microscope apparatus of the present invention, as described above. Photographs of images derived from the above apparatus are included in FIGS. 3, 4, and 5, and reference should be made thereto. The microscope utilized was a Digital Instruments Nanoscope III using a blue diamond probe. The sample utilized was a GaAs semiconductor wafer that was polished prior to testing. The force sensor scale factor was 5.59 V/gram, and the scanning tunneling microscope set point was 200 pA.

Figure 3:
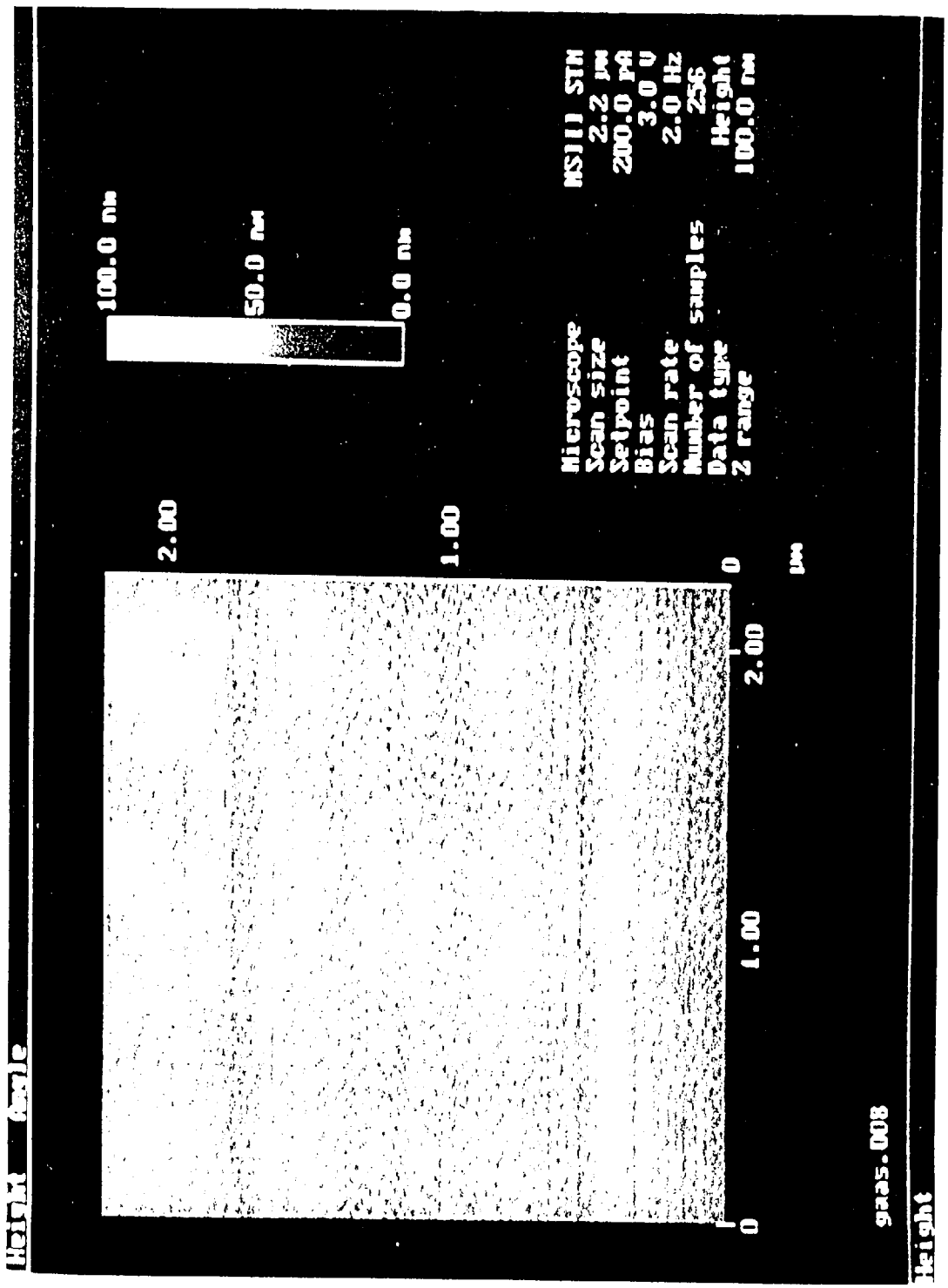
FIG. 3 is a photograph of an image display of the topography of a sample prior to hardness testing on an apparatus of the present invention.
Figure 4:
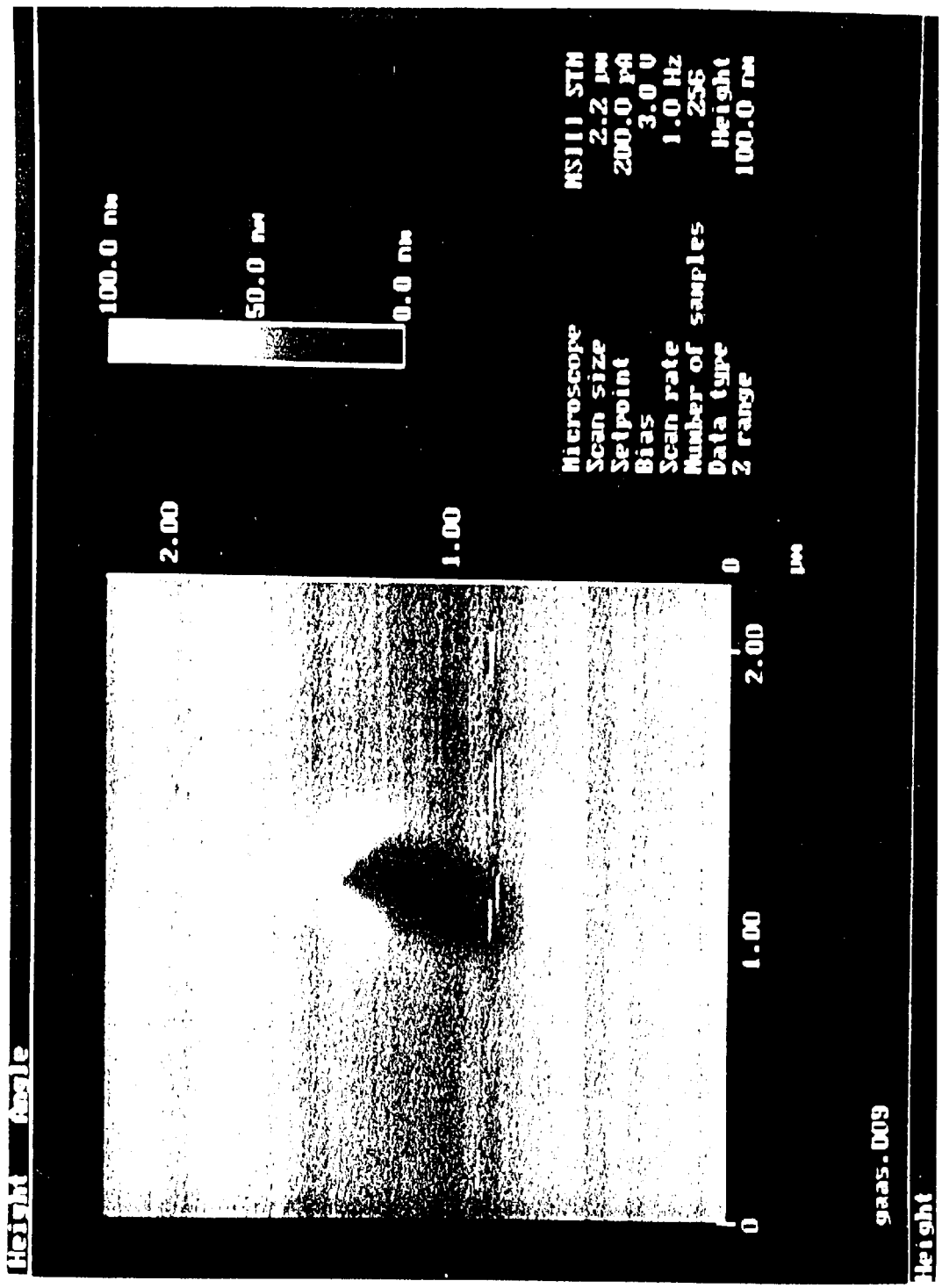
FIG. 4 is a photograph of an image display of the topography of a sample subsequent to hardness testing on an apparatus of the present invention.
Figure 5:
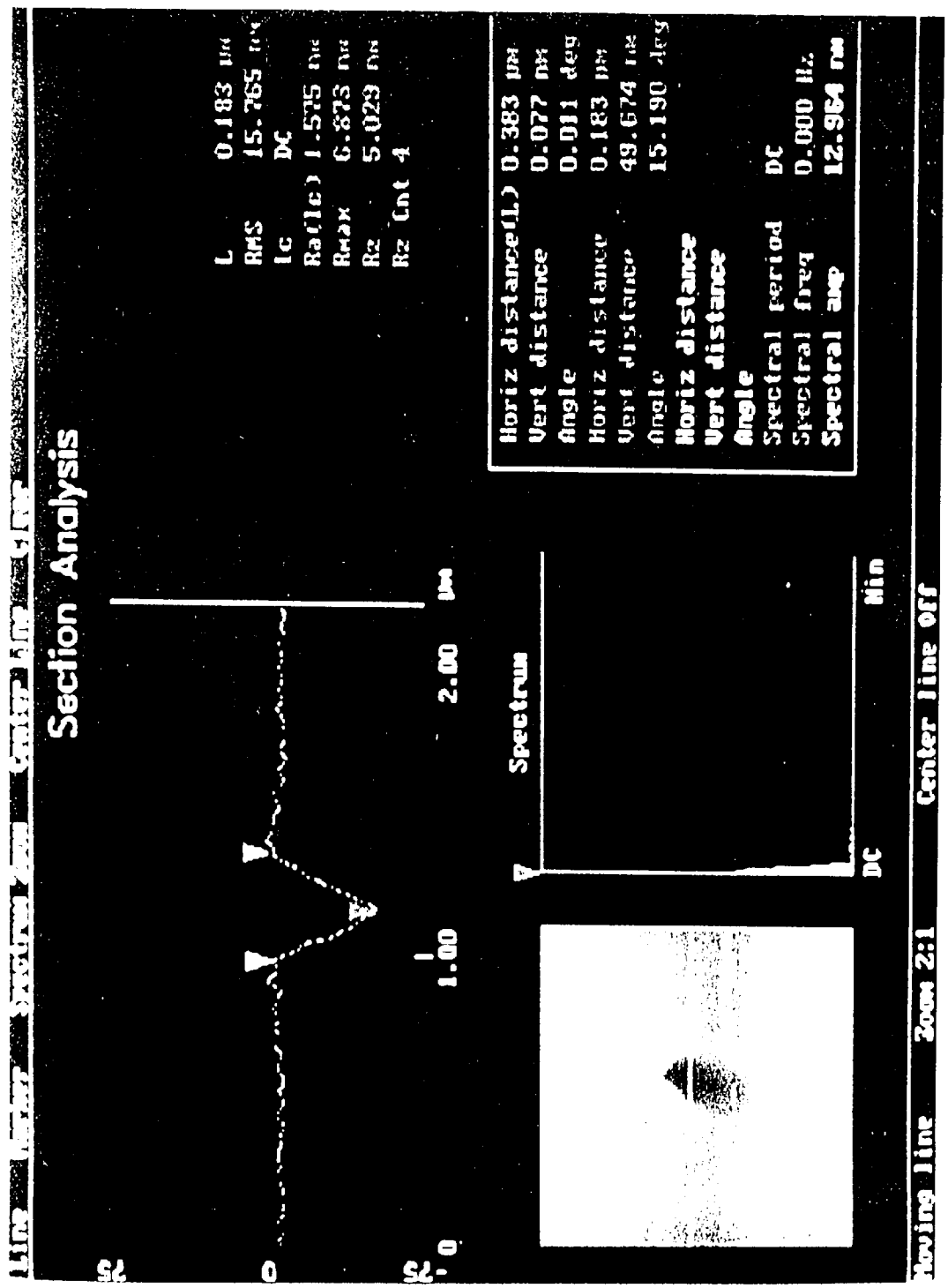
FIG. 5 is a photograph of the image display of FIG. 4, including sectional analysis of a sample subsequent to hardness testing.

The image of FIG. 3 was taken before indenting while the image in FIG. 4 was taken after applying a force of 77.8 mg. The surface topography, as affected by the indentation, is evident from the recorded image variation in color. The rust to dark brown area clearly showing the deepest indentation. The third image or FIG. 5 is a sectional analysis of the indent of FIG. 4 at its deepest section. The relevant data is the horizontal distance in red of 0.383 micrometers and the vertical distance in green of 0.0497 micrometers.

The operating force during imaging is determined to be the combination of the sensor scale factors, the current to voltage conversion factor for the microscope, and the tunneling current setpoint. For the above scanning tunneling microscope, the factor was 0.1 V/nA so with the set point of 200 pA, the instrument would apply whatever force was required to produce 20 millivolts which is the equivalent of 3.58 milligrams force. Due to a 5 millivolt offset error somewhere in the system in the above tests, the 200 pA setpoint generated a 15 mV, rather than 20 mV for sensor output and the force sensor had an output of 10 mV at 0 load, so the actual load was about 0.89 mg. These offsets can be corrected with adjustments to the setpoint of the scanning tunneling microscope.

The apparatus for microindentation hardness testing of surface imaging of the present invention has been described with respect to a preferred embodiment in which a scanning tunneling microscope apparatus is utilized having a base for mounting a sample thereon and a piezo actuated head having a probe mounted thereon for operative engagement of a sample mounted on the base for measuring surface typography. In this embodiment, a probe is mounted on the piezo actuated head, while the force sensor is mounted on the base for mounting a sample thereon. With this arrangement, the scanning head or piezo actuated head moves the probe in a raster pattern over the surface dimension typography. It is, however, recognized that other arrangements of the probe, force sensor and scanning head are possible within the scope of the present invention. The key to operation of applicant's invention is that a scanned probe microscope apparatus incorporates a probe in a scanning head arranged for operative engagement of a surface of a sample for measuring a surface typography thereof. The probe has a hardness greater than a sample to be tested and the force sensor is operatively located to measure the force between the sample and the probe when operatively engaged in the surface thereof.

Figure 2C:
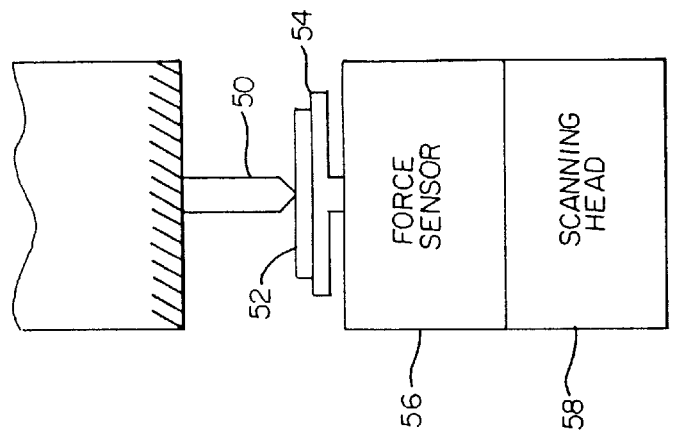
FIG. 2C is a fourth alternative embodiment showing the probe mounted to a fixed surface and the sample mounted to the force sensor and further mounted to the scanning head.

As previously stated, in a first preferred embodiment, scanned probe microscope includes a base for mounting a sample thereon and a piezo actuated head having a probe mounted thereon, with the force sensor mounted on the base 5 and the sample resting thereon. In a second preferred embodiment, as shown in FIG. 2A, the force sensor may be mounted on a fixed surface with the probe affixed to the force sensor. The sample may be mounted on a sample holder which incorporates a piezo actuated head or scanning head. With this arrangement, the piezo actuated scanning head moves the sample against the probe with the force applied to the probe translated through the sensor to measure the force.

Figure 2B:
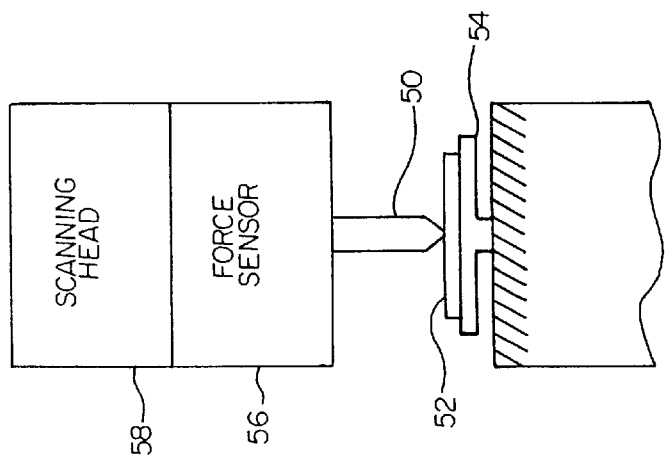
FIG. 2B is a third alternative embodiment showing the probe mounted on the sensor and the sensor mounted on the scanning head.
Figure 2A:
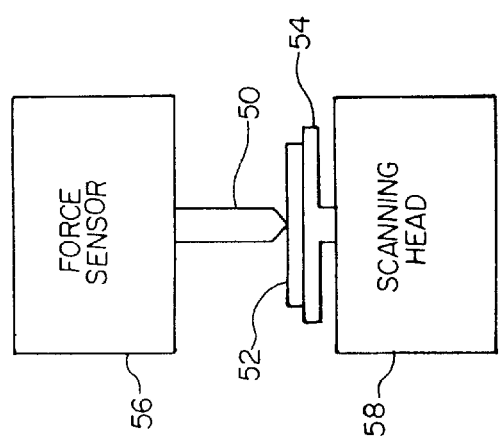
FIG. 2A shows a probe mounted to a force sensor which interacts with a sample mounted upon a scanning head.

In a third alternative embodiment, as shown in FIG. 2B, the sample having a surface to be scanned may be a large sample on which an instrument of the present invention may be mounted. The instrument would include the probe mounted on the force sensor, which in turn is mounted on the piezo actuated or scanning head. With this arrangement, the probe is placed to engage the surface of the large sample and the force sensor is again utilized to measure the force of contact, while the scanning head moves the probe over the surface for imaging.

In a fourth alternative embodiment, as shown in FIG. 2C, the probe can be mounted on a fixed surface. With this arrangement, the sample and force sensor are mounted on the piezo actuated or scanning head. Thus, the scanning head moves the sample over the fixed probe with the sensor measuring the force between such probe and sample.

New characteristics and advantages of the invention covered by this document have been set forth in the foregoing description. It will be understood, however, that this disclosure is, in many ways, only illustrative. Changes may be made in details, particularly in matters of shape, size, and arrangement of parts, without exceeding the scope of the invention. The scope of the invention is, of course, defined in the language in which the appended claims are expressed.

What is claimed:

1. In a scanned probe microscope apparatus having a probe and a scanning head operably arranged for measuring surface properties of a sample, the apparatus improvement comprising:
   a high precision capacitance sensor having a pick-up plate movably mounted relative to a drive plate;
   means for transmitting force between an object remote from the pick-up plate and the pick-up plate; and
   means responsive to the position of the pick-up plate relative to the drive plate for providing an output signal proportional to the relative position.

2. The apparatus of claim 1, wherein the means for transmitting force between an object remote from the pick-up plate and the pick-up plate includes the pick-up plate mechanically linked to the probe.

3. The apparatus of claim 1, wherein the means responsive to the position of the pick-up plate relative to the drive plate includes means for utilizing said output signal to control a vertical movement of the scanning head relative to the sample.

4. The apparatus of claim 3, wherein the vertical movement of the scanning head relative to the sample is controlled to maintain a constant force on the sample as the surface property is measured.

5. The apparatus of claim 1, wherein the means responsive to the position of the pick-up plate relative to the drive plate includes means for applying an AC signal to the drive plate.

6. The apparatus of claim 1, wherein the means responsive to the position of the pick-up plate relative to the drive plate synchronously demodulates the output signal to produce a DC signal proportional to the displacement of the pick-up plate.

7. In a scanned probe microscope apparatus having a probe and a scanning head arranged for operative engagement of the surface of a sample for measuring a surface property thereof, the apparatus improvement comprising:
   a force sensor operatively located to measure the surface property, the force sensor having an output signal representative of the measured surface property, wherein the force sensor includes:
      a pair of capacitive transducers, each transducer including a separate drive plate and a shared pick-up plate movably suspended between the drive plates, wherein said pick-up plate is capable of deflection between each of the drive plates; and
      means for transmitting force from a point remote from the pick-up plate to the pick-up plate.

8. The apparatus of claim 7, further comprising means for measuring the output signal of the force sensor and utilizing the output signal to control a vertical movement of the scanning head.

9. The apparatus of claim 8, wherein the vertical movement of the scanning head is controlled to maintain a constant force on the sample as the surface topography is measured.

10. The apparatus of claim 8, further comprising means for applying a downward force to said probe, wherein said force sensor measures the force and the means for measuring the output signal of the force sensor converts the output signal to a signal representative of the force during an indentation test.

11. The apparatus of claim 7, further comprising means responsive to the output signal for controlling the movement of the scanning head.

12. The apparatus of claim 11, wherein the movement of the scanning head is controlled in a vertical direction.

13. The apparatus of claim 12, wherein the means responsive to the output signal further controls the movement of the scanning head in a two-dimensional horizontal direction.

14. The apparatus of claim 13, wherein the means for controlling movement of the scanning head provides an output signal to an image display, wherein the image display provides an image representative of the surface property being measured.

15. The apparatus of claim 7, further comprising means responsive to the output signal for providing an image representative of the surface topography.

16. In a high resolution sensor apparatus for use with a scanned-probe microscope having a probe and a scanning head operably arranged for measuring surface properties of a sample, the apparatus improvement comprising:
   a. a sensor element, said sensor element including,
      1. a pair of capacitive transducers, each transducer including a separate drive plate, and a shared pickup plate, said pickup plate positioned between said separate drive plates, said drive plates having spaced opposing conductive surfaces when said pickup plate is mounted therebetween, said pickup plate further comprising a conductive central plate suspended by spring means between said drive plates, wherein said central plate is capable of deflection between the conductive surfaces of each of said drive plates;
      2. means for mechanically transmitting force from a point remote from said central plate to said central plate; and
   b. means for providing an output signal representative of the surface property being measured, including means for applying an alternating current carrier signal to said pair of drive plates, wherein the signal to one of said drive plates is 180 degrees out of phase with the signal to the other of said drive plates.

17. The apparatus of claim 16, further comprising means for measuring the output signal of the sensor element and utilizing the output signal to control a vertical movement of the scanning head.

18. The apparatus of claim 17, wherein the vertical movement of the scanning head is controlled to maintain a constant force on the sample as the surface topography is measured.

19. The apparatus of claim 16, further comprising means for applying a downward force to said probe, wherein said sensor element measures the force and the means for measuring the output signal of the sensor element converts the output signal to a signal representative of the force during an indentation test.

20. The apparatus of claim 16, further comprising means responsive to the output signal for controlling the movement of the scanning head.

21. The apparatus of claim 20, wherein the movement of the scanning head is controlled in a vertical direction.

22. The apparatus of claim 21, wherein the means responsive to the output signal further controls the movement of the scanning head in a two-dimensional horizontal direction.

23. The apparatus of claim 22, wherein the means for controlling movement of the scanning head provides an output signal to an image display, wherein the image display provides an image representative of the surface property being measured.

24. The apparatus of claim 16, further comprising means responsive to the output signal for providing an image representative of the surface topography.

* * * * *

(12) EX PARTE REEXAMINATION CERTIFICATE (6686th)
United States Patent
Bonin

(10) Number: US 6,026,677 C1
(45) Certificate Issued: *Mar. 3, 2009

(54) APPARATUS FOR MICROINDENTATION HARDNESS TESTING AND SURFACE IMAGING INCORPORATING A MULTIPLATE CAPACITOR SYSTEM

(75) Inventor: Wayne A. Bonin, North Oaks, MN (US)

(73) Assignee: Hysitron Incorporated, Minneapolis, MN (US)

Reexamination Request:
No. 90/008,670, Jun. 3, 2007

Reexamination Certificate for:
Patent No.: 6,026,677
Issued: Feb. 22, 2000
Appl. No.: 08/965,332
Filed: Nov. 6, 1997

(*) Notice: This patent is subject to a terminal disclaimer.

Related U.S. Application Data

(63) Continuation of application No. 08/690,909, filed on Aug. 1, 1996, now abandoned, which is a continuation of application No. 08/327,979, filed on Oct. 24, 1994, now Pat. No. 5,553,486, which is a continuation-in-part of application No. 08/131,405, filed on Oct. 1, 1993, now abandoned.

(51) Int. Cl.
*G01N 3/42* (2006.01)
*G01N 3/40* (2006.01)
*G01P 15/125* (2006.01)
*G01G 7/06* (2006.01)
*G01G 7/00* (2006.01)

(52) U.S. Cl. .................. 73/105; 73/862.626; 361/283.2; 361/283.3; 361/283.4

(58) Field of Classification Search .................. None
See application file for complete search history.

(56) References Cited

U.S. PATENT DOCUMENTS

| 4,669,300 A | 6/1987 | Hall et al. |
| 4,694,687 A | 9/1987 | Bonin et al. |
| 4,800,274 A | 1/1989 | Hansma et al. |
| 4,848,141 A | 7/1989 | Oliver et al. |
| 4,896,100 A | 1/1990 | Buck |
| 5,085,070 A | 2/1992 | Miller et al. |
| 5,146,690 A | 9/1992 | Breitmeier |
| 5,224,376 A | 7/1993 | Elings et al. |
| 5,336,887 A | 8/1994 | Yagi et al. |

FOREIGN PATENT DOCUMENTS

| EP | 0290648 A1 | 11/1988 |
| EP | 0407835 A2 | 7/1989 |
| JP | 02-239432 | 9/1990 |

OTHER PUBLICATIONS

Patent Abstracts of Japan for Pub. No. 02–239432.
Partial English Translation of JP Pub. No. 02–239432.

(Continued)

*Primary Examiner*—Deandra M Hughes

(57) ABSTRACT

A force, weight or position sensor unit and sensor element incorporated into an apparatus for microindentation hardness testing and surface imaging which allows immediate imaging of the surface subsequent to hardness testing. The sensor uses a multi-capacitor system having drive and pick-up plates mounted on an appropriate suspension system to provide the desired relative motion when a force is applied to the pick-up plate. The output signal is run through a buffer amplifier and synchronously demodulated to produce a signal proportional to force or displacement. The sensor element is mounted on a scanning tunneling microscope base and a sample mounted on the sensor. The force sensor is used for both measuring the applied force during microindentation or micro hardness testing and for imaging before and after the testing to achieve an atomic force microscope type image of the surface topography before and after indentation testing.

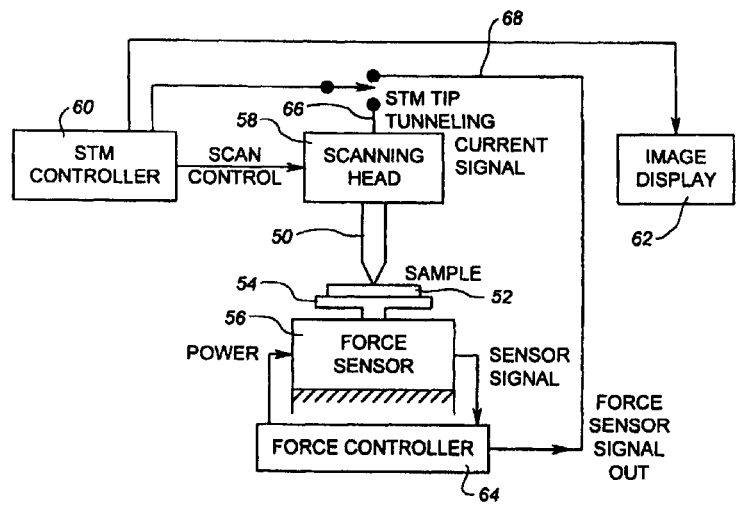

OTHER PUBLICATIONS

"Notification of Reasons for Refusal" Pat. Appln. No. 2007–241895 with English Translation.

Plaintiff's Prior Art Statement, Civil No. 07–cv–1533 (ADM/AJB).

Defendant's Prior Art Statement, Civil No. 07–cv–01533 (ADM/AJB).

Todd, J.D. and Pethica, J.B., A Sheer Model for STM Imaging of Layered Material, J. Phys.: Condens. Matter 1, pp. 9823–9831 (1989).

Pethica, J.B. and Oliver, W.C., Tip Surface Interactions in STM and AFM, Physica Scripta, vol. 119, pp. 61–67 (1987).

Burnham N.A. and Colton R.J., Measuring the nanomechanical properties and surface forces of materials using an atomic force microscope, J. Vac. Sci. Technol, p. 2906–2913, Jul./Aug. 1989.

"Tip Surface Interactions with STM and AFM", J.B. Pethica and W.C. Oliver, Physica Scripta. vol. 119, 61–66, 1987.

"A shear model for STM imaging of layer materials", J.D. Todd and J.B. Pethica, J. Phys.; Condenc. Matteer 1 (1989) 9823–9831.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–24 is confirmed.

* * * * *